(12) United States Patent
Pingree, Jr. et al.

(10) Patent No.: US 8,119,413 B2
(45) Date of Patent: Feb. 21, 2012

(54) METHOD AND SYSTEM FOR DETECTION OF SOLID MATERIALS IN A PLASMA USING AN ELECTROMAGNETIC CIRCUIT

(75) Inventors: Richard E. Pingree, Jr., New Market, MD (US); Palanikumara Sakthivel, Gaithersburg, MD (US); Mahesh Vanodia, Germantown, MD (US); Michael B. Colson, Woodbine, MD (US)

(73) Assignee: Axcelis Technologies, Inc., Beverly, MA (US)

(*) Notice: Subject to any disclaimer, the term of this patent is extended or adjusted under 35 U.S.C. 154(b) by 0 days.

(21) Appl. No.: 12/843,175

(22) Filed: Jul. 26, 2010

(65) Prior Publication Data
US 2010/0289510 A1 Nov. 18, 2010

Related U.S. Application Data

(62) Division of application No. 10/708,251, filed on Feb. 19, 2004, now Pat. No. 7,794,663.

(51) Int. Cl.
*G01N 27/02* (2006.01)

(52) U.S. Cl. ...... 436/149; 73/23.2; 73/335.03; 204/155; 204/554; 204/556; 324/263; 324/600; 324/71.1

(58) Field of Classification Search ............ 73/23.2, 73/335.03; 436/179; 204/155, 554, 556; 324/263, 600, 71.1
See application file for complete search history.

(56) References Cited

U.S. PATENT DOCUMENTS

| | | | |
|---|---|---|---|
| 3,569,777 A | 3/1971 | Harvey | |
| 3,931,587 A | 1/1976 | Harp et al. | |
| 4,207,137 A | 6/1980 | Tretola | |
| 4,608,869 A | 9/1986 | Lerner | |
| 4,685,802 A | 8/1987 | Saito et al. | |
| 4,711,767 A | 12/1987 | Diederich | |
| 4,926,120 A | 5/1990 | Veronesi et al. | |
| 5,079,507 A | 1/1992 | Ishida et al. | |
| 5,103,181 A | 4/1992 | Gaisford et al. | |
| 5,419,176 A | 5/1995 | Walker | |
| 5,467,188 A | 11/1995 | Miyashita | |
| 5,471,357 A | 11/1995 | Ishizuka | |
| 5,479,254 A | 12/1995 | Woskov et al. | |
| 5,517,161 A | 5/1996 | Andersson et al. | |
| 5,531,097 A | 7/1996 | Tsuchida et al. | |
| 5,631,418 A | 5/1997 | Stuns et al. | |
| 5,691,642 A | 11/1997 | Dobkin | |
| 5,708,209 A | 1/1998 | Stiffler et al. | |
| 5,742,234 A | 4/1998 | Owen | |
| 5,939,886 A | 8/1999 | Turner et al. | |

(Continued)

OTHER PUBLICATIONS

Advisory Action for U.S. Appl. No. 10/708,251, filed Feb. 19, 2004; First Named Inventor; Richard E. Pingree, Jr. Mail Date: Feb. 21, 2008.

(Continued)

*Primary Examiner* — Jill Warden
*Assistant Examiner* — Monique Cole
(74) *Attorney, Agent, or Firm* — Cantor Colburn LLP

(57) ABSTRACT

A method for solid material detection in a medium includes receiving an exhaust gas downstream with respect to a workpiece from which a photoresist material is removed. An electromagnetic circuit is configured to include the exhaust gas, the exhaust gas is excited with electromagnetic energy and an impedance value of the electromagnetic circuit is determined, wherein the impedance value corresponds to an amount of solid material within the exhaust gas.

13 Claims, 8 Drawing Sheets

U.S. PATENT DOCUMENTS

| | | | |
|---|---|---|---|
| 5,987,972 | A | 11/1999 | Hirota et al. |
| 6,081,329 | A | 6/2000 | Cohn et al. |
| 6,377,345 | B1 | 4/2002 | Powell |
| 6,429,935 | B1 | 8/2002 | Duan |
| 6,543,459 | B1 | 4/2003 | Annapragada |
| 6,614,215 | B1 | 9/2003 | Wood |
| 6,630,406 | B2 | 10/2003 | Waldfried et al. |
| 7,004,107 | B1 * | 2/2006 | Raoux et al. ............. 118/723 E |
| 2004/0118348 | A1 | 6/2004 | Mills |
| 2004/0135590 | A1 | 7/2004 | Quon |
| 2004/0235299 | A1 | 11/2004 | Srivastava et al. |

OTHER PUBLICATIONS

Advisory Office Action for U.S. Appl. No. 10/708,251, filed Feb. 19, 2004; First Named Inventor: Richard E. Pingree, Jr. Mail Date: Feb. 24, 2010.

Somlo, P.I. and Hunter, J.D. "Microwave Impedance Measurement" (IEE Electrical Measurement Series, No. 2; Dec. 1985, pp. 110-111 & 120.

Final Office Action for U.S. Appl. No. 10/708,251, filed Feb. 19, 2004; First Named Inventor: Richard E. Pingree, Jr. Mail Date: Dec. 8, 2009.

Final Office Action for U.S. Appl. No. 10/708,251, filed Feb. 19, 2004; First Named Inventor: Richard E. Pingree, Jr. Mail Date: Nov. 28, 2007.

Final Office Action for U.S. Appl. No. 10/708,251, filed Feb. 19, 2004; First Named Inventor: Richard E. Pingree, Jr. Mail Date: Dec. 8, 2009.

Non-Final Office Action for U.S. Appl. No. 10/708,251, filed Feb. 19, 2004; First Named Inventor: Richard E. Pingree, Jr. Mail Date: Feb. 2, 2009.

Non-Final Office Action for U.S. Appl. No. 10/708,251, filed Feb. 19, 2004; First Named Inventor: Richard E. Pingree, Jr. Mail Date: Mar. 31, 2008.

Non-Final Office Action for U.S. Appl. No. 10/708,251, filed Feb. 19, 2004; First Named Inventor: Richard E. Pingree, Jr. Mail Date: Jul. 10, 2007.

Notice of Allowance for U.S. Appl. No. 10/708,251, filed Feb. 19, 2004; First Named Inventor: Richard E. Pingree, Jr. Mail Date: Jun. 1, 2010.

Restriction/Election Office Action for U.S. Appl. No. 10/708,251, filed Feb. 19, 2004; First Named Inventor: Richard E. Pinegree, Jr. Mail Date: Jun. 7, 2007.

* cited by examiner

METHOD AND SYSTEM FOR DETECTION OF SOLID MATERIALS IN A PLASMA USING AN ELECTROMAGNETIC CIRCUIT

CROSS REFERENCE TO RELATED APPLICATIONS

This application is a divisional of the legally related U.S. application Ser. No. 10/708,251, filed Feb. 19, 2004, which is fully incorporated herein by reference.

BACKGROUND

The present disclosure relates generally to detection of solid materials and, more particularly, to a method and system for detection of solid materials in semiconductor manufacturing apparatuses and processes using an electromagnetic circuit, such as a microwave circuit or a radio frequency (RF) circuit.

Recently, much attention has been focused on developing low-k dielectric thin films for use in the next generation of microelectronics. As integrated devices become smaller, the RC-delay time of signal propagation along interconnects becomes one of the dominant factors limiting overall chip speed. With the advent of copper technology, circuit resistance has been pushed to its practical lowest limit for current state of the art, so attention must be focused on reducing capacitance. One way of accomplishing this task is to reduce the average dielectric constant (k) of the thin insulating films surrounding interconnects. The dielectric constant of traditional silicon dioxide insulative materials is about 3.9. Thus, lowering the dielectric constant below 3.9 will provide a reduced capacitance.

Low-k dielectric materials used in advanced integrated circuits typically comprise organic polymers or oxides, and have dielectric constants less than about 3.5. The low-k dielectric materials may be spun onto the substrate as a solution or deposited by a chemical vapor deposition process. Certain low-k film properties include thickness and uniformity, dielectric constant, refractive index, adhesion, chemical resistance, thermal stability, pore size and distribution, coefficient of thermal expansion, glass transition temperature, film stress, and copper diffusion coefficient.

In fabricating integrated circuits on wafers, the wafers are generally subjected to many process steps before finished integrated circuits can be produced. One such process step is what is known as "ashing." Ashing refers to a plasma-mediated stripping process by which photoresist and post etch residues are stripped, ashed or removed from a substrate upon exposure to the plasma. The ashing process generally occurs after an etching (front-end-of-line or back-end-of-line) or implant process (front-end-of-line) has been performed in which a photoresist material is used as a mask for etching a pattern into the underlying substrate, or for selectively implanting ions into the exposed areas of the substrate. Any remaining photoresist (as well as any post etch or post implant residues on the wafer after the etch process or implant process is complete) must be removed prior to further processing, for numerous reasons generally known to those skilled in the art. The ashing step is typically followed by a wet chemical treatment to remove traces of the residue, which can cause further degradation or loss of the underlying substrate. In the case of low-k dielectric substrates, material degradation, loss of material, and an increase in the dielectric constant may also result.

Ideally, the ashing plasma should not affect the underlying low-k dielectric layers, and preferably removes only the photoresist material. The use of silicon dioxide ($SiO_2$) as a dielectric material has heretofore provided high selectivity with respect to traditional ashing gas sources. Typically, the ashing or burning of organic material, such as photoresist on a semiconductor substrate like silicon (Si) is implemented through the use of an oxygen or nitrogen-based plasma chemistry. However, low-k dielectric materials, especially carbon containing low-k dielectric materials, can be sensitive to this type of process step. More specifically, the conventional plasma chemistry used during ashing can strip both the photoresist materials, as well as remove a portion of a low-k dielectric film.

One approach that implements an oxygen and nitrogen-free photoresist removal chemistry is disclosed in U.S. application Ser. No. 09/855,177, assigned to the assignee of the present application, and incorporated herein by reference in its entirety. As discussed therein, while the oxygen and nitrogen-free chemistry is not damaging to the low-k material and can successfully remove the photoresist, the actual mechanism of photoresist removal is different from that of the conventional oxygen or nitrogen based ashing chemistry. Conventional ashing is a process in which the photoresist is typically completely volatilized into OH and CO, which emit light at their characteristic wavelengths. As such, an endpoint of the ashing process may be detected by simply monitoring the intensity of these light emissions until they disappear.

In contrast, the removal mechanism discussed in the '177 application (e.g., plasma formed from helium and hydrogen) involves a partial sublimation of the photoresist material, which thereafter has a tendency to rapidly re-solidify. The net effect is the introduction of solid and semi-solid materials into the gas as it gets pumped out. However, since there is no light emitted in this type of a reaction, end-point detection becomes a difficult task. In addition, as a result of the mechanism of removal, the plasma exposure tends to deposit large amounts of the sublimed photoresist and byproducts within the processing chamber and in areas downstream from the plasma process chamber, such as in the throttle valve and exhaust lines.

Accordingly, there exists a need for detecting the presence and relative amounts of solid material and semi-solid material entrained in a medium, such as sublimed photoresist in a helium-hydrogen gas mixture, resulting from removal processes suited for low-k applications.

BRIEF SUMMARY

The foregoing discussed drawbacks and deficiencies of the prior art are overcome or alleviated by a method for detection of solid material present within a medium of interest. In an exemplary embodiment, the method includes configuring the medium of interest within an electromagnetic circuit, exciting the medium of interest using electromagnetic energy, and determining an impedance value of the electromagnetic circuit, wherein the impedance value corresponds to an amount of solid material within the medium of interest.

In another aspect, a method for solid material detection in a photoresist removal system includes receiving an exhaust gas downstream with respect to a workpiece from which a photoresist material is removed. An electromagnetic circuit is configured to include the exhaust gas, the exhaust gas is excited with electromagnetic energy, and an impedance value of the electromagnetic circuit is determined, wherein the impedance value corresponds to an amount of solid material within the exhaust gas.

In still another aspect, a material detection system includes a flow path configured to contain a medium of interest in which solid material is to be detected. An electromagnetic energy source is configured for exciting the medium of interest, and an impedance measuring device is configured for measuring an impedance value of a electromagnetic circuit, the electromagnetic circuit including the flow path therein, wherein the impedance value corresponds to an amount of solid material within the medium of interest.

In still another aspect, a plasma based semiconductor material removal system includes an upstream electromagnetic energy source configured to cause excitation of an input gas into a plasma so as to produce a reactive species. The system further includes a mechanism for uniformly conveying the reactive species to a surface of a workpiece having photoresist material formed thereupon, and a mechanism for heating the workpiece so as to enhance the reaction rate of the photoresist material and the reactive species. A downstream electromagnetic energy source is configured for exciting an exhaust gas downstream of the workpiece, and an impedance measuring device is configured for measuring an impedance value of an electromagnetic circuit, the electromagnetic circuit including the exhaust gas therein, wherein the impedance value corresponds to an amount of solid material within the exhaust gas.

In still another aspect, a method for implementing material removal from a semiconductor workpiece includes receiving exhaust gas containing material removed from the workpiece. A first power level is applied to an electromagnetic circuit, the electromagnetic circuit containing the exhaust gas therein, wherein said first power level is sufficient to volatize solid material contained within the exhaust gas. A second power level is applied to the microwave circuit for a selected duration, and, during the selected duration, the electromagnetic circuit is used to detect the presence of remaining solid material within the exhaust gas.

The above described and other features are exemplified by the following figures and detailed description.

BRIEF DESCRIPTION OF THE DRAWINGS

Referring to the exemplary drawings wherein like elements are numbered alike in the several Figures.

DETAILED DESCRIPTION

Disclosed herein is a method and system for quantitative detection of small amounts of solid or semi-solid material entrained in a medium of interest, such as a gas or plasma. Solid or semi-solid "materials" discussed hereinafter generally refer to particulate matter and "chunks" that may be as small as a few nanometers, but less than about 5 mm in size, such as may be entrained in a flowing fluid medium. For example, in the case of photoresist material, the solid matter is made of long chains of cross-linked organic molecules. Accordingly, one example of a suitable application for such a method is in the area of semiconductor manufacturing equipment, wherein plasma technology is ubiquitous and used for many tasks such as etching, ashing and deposition of thin films.

One way to generate this plasma is through the use of electromagnetic radiation. As described hereinafter, the term "electromagnetic" may refer to specific frequency regions of the electromagnetic spectrum, such as the microwave range and the radio frequency (RF) range, for example. Heretofore, the (microwave) plasma has been generated upstream with respect to a semiconductor substrate, in order to initiate controlled reactions thereupon. In contrast, the present disclosure utilizes a second, separate downstream-generated microwave plasma to detect solid matter that may be entrained in the effluent (i.e., removal byproducts), resulting from the material removal process.

Since both the gas and solid material are part of an electromagnetic (e.g., microwave) circuit, a quantitative response in the circuit impedance corresponding to the amount of solid material present in the gas may be obtained. As used hereinafter, the term "impedance" refers to, or may be described, measured or otherwise obtained in terms of resistance/reactance in one coordinate system. Alternatively, "impedance" may also refer to or be described/measured/obtained in terms of phase/magnitude (i.e., the reflection coefficient) in another coordinate system. As is also discussed in further detail hereinafter, the time-resolved reflection coefficient of the microwave circuit demonstrates excellent correlation with the time-resolved intensities of optical emissions from the solid material (also caused by the microwave excitation), thereby establishing a desirable alternative to optical endpoint detection approaches. One such alternative endpoint detection approach is described in U.S. application Ser. No. 10/249,964, assigned to the assignee of the present application, the contents of which are incorporated herein in their entirety. Although the embodiments described hereinafter are discussed in terms of plasma excited at a microwave frequency range of the electromagnetic spectrum, it should again be understood that the impedance/reflection coefficient detection principles presented herein are equally applicable to other regions of the EM spectrum, such as radio frequency (RF) based systems, for example.

Figure 1:
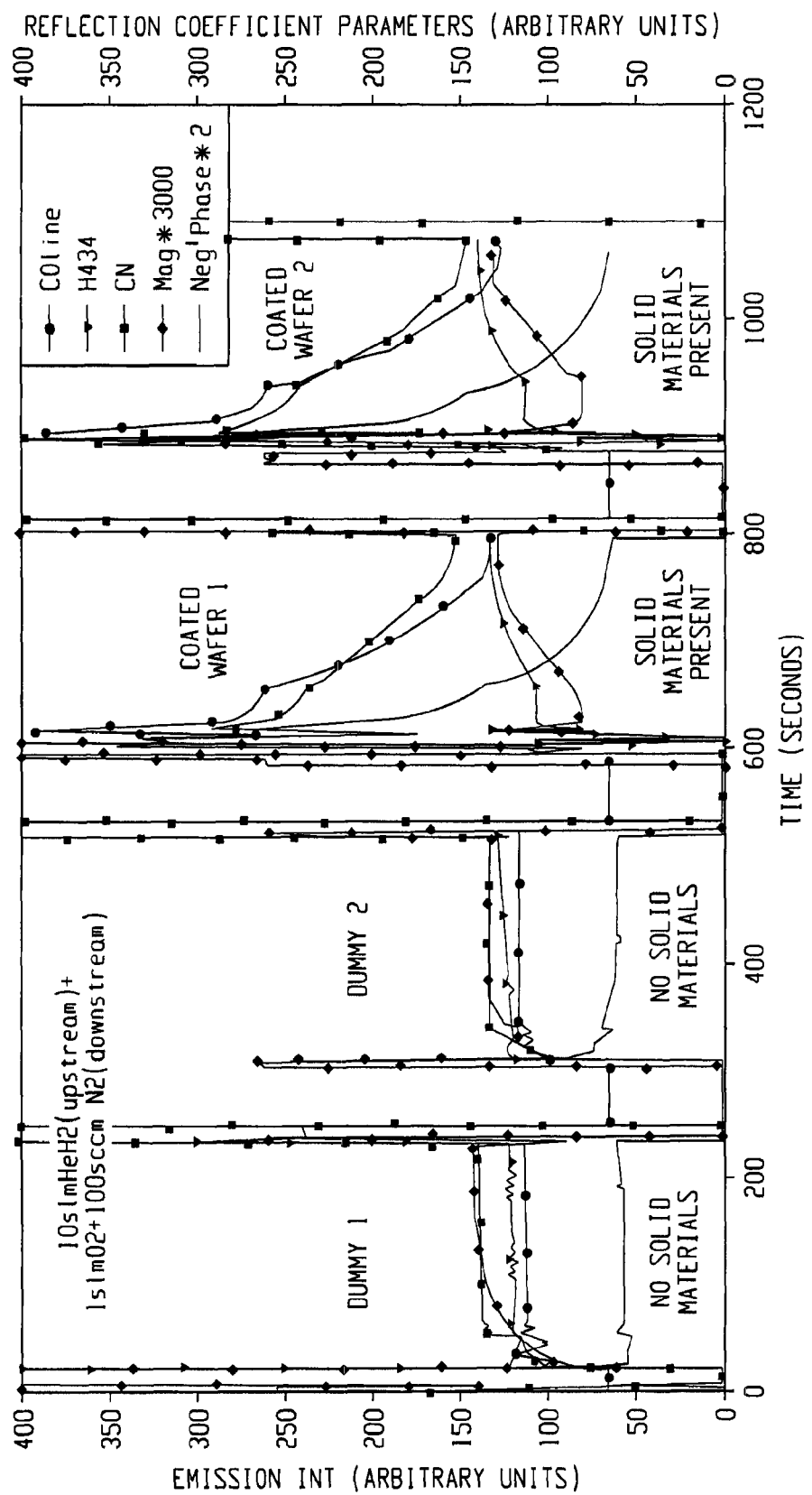
FIG. 1 is a graph including a series of comparative plots that demonstrate a correlation between emission signal intensities determined from conventional, optical endpoint detection techniques and from microwave circuit reflection coefficient measurements on four separate workpieces.

Referring initially to FIG. 1, there is shown a series of comparative plots that demonstrate a correlation between emission signal intensities determined from optical endpoint detection techniques plotted on the left y-axis, and normalized reflection coefficient phase and magnitude values (plotted on the right y-axis) determined at a selected point within a microwave circuit established by the application of downstream plasma. More specifically, FIG. 1 includes a comparison of five curves, including a normalized quantity of optically detected CO species and CN species (photoresist removal byproducts), a quantity of detected hydrogen species at a wavelength of 434 nanometers, the measured magnitude of microwave circuit reflection coefficient, and the measured phase of the reflection coefficient.

Figure 2:
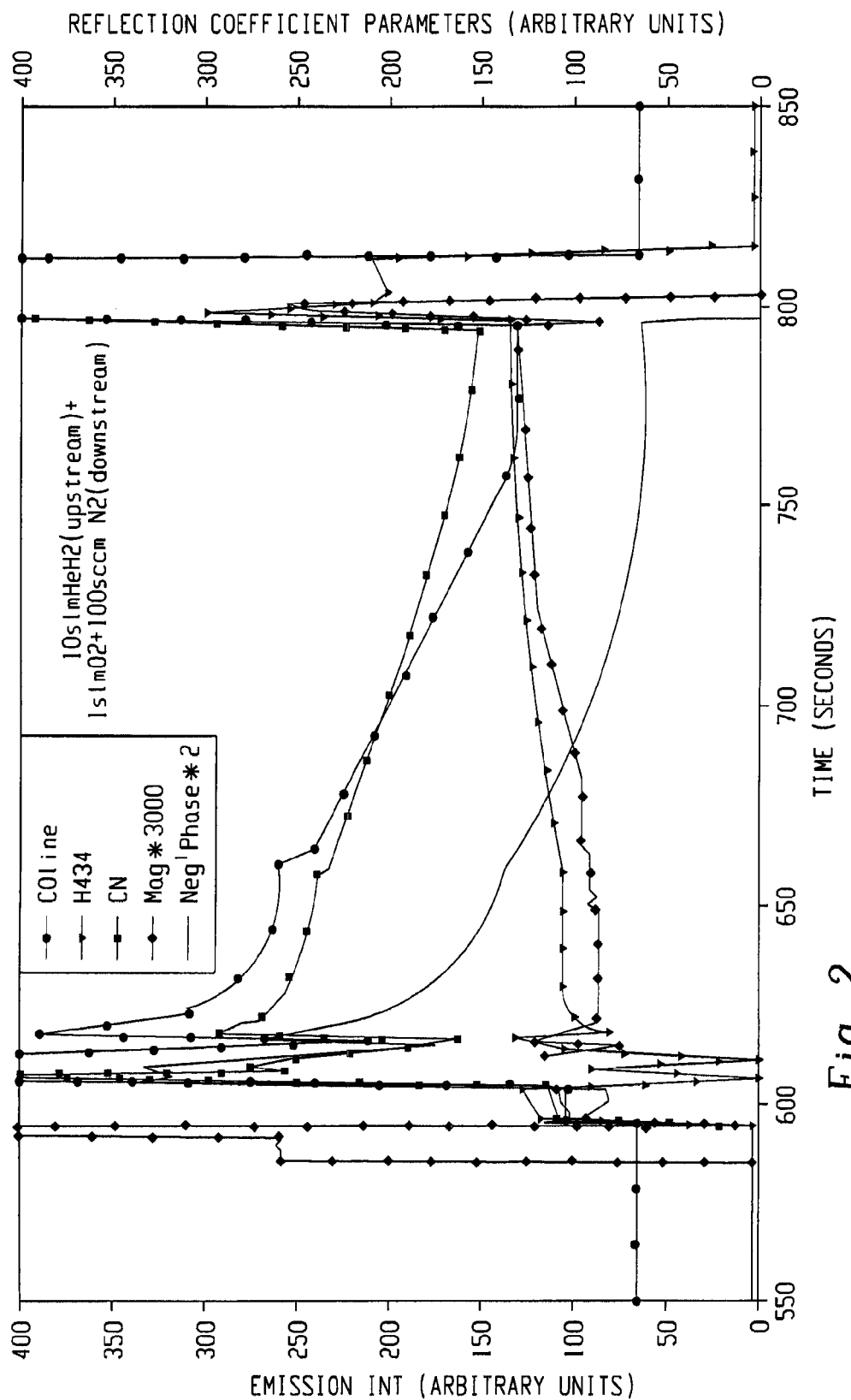
FIG. 2 is a magnified view of one of the plots shown in the graph of FIG. 1.

The first two plots (designated as "dummy 1 and dummy 2" in FIG. 1) reflect results obtained during two "dummy trials" wherein upstream plasma excitation and subsequent downstream excitation were carried out without any photoresist material actually present on the subject semiconductor wafer. Accordingly, as can be seen in FIG. 1, there is no substantial change in emission signal intensities from baseline levels for the CO and CN products that would otherwise occur in an actual resist removal process. However, as shown for the subsequent two trials (designated "coated wafer 1" and "coated wafer 2" in FIG. 1), the magnitude of the signal intensity of the optically detected photoresist species demonstrates an upward trend as the amount of solid material (photoresist in this example) decreases, as is the case with the signal resulting from the hydrogen radical at a wavelength of 434 nm. The phase signal portion of the reflection coefficient measurement also shows a simultaneous downward trend, like the CO and CN emission signal intensities. A magnified view of the "coated wafer 1" trial is shown in FIG. 2.

The plots designated "coated wafer 1" and "coated wafer 2" in FIG. 1 were obtained using a microwave power of 300 W, which resulted in a coating of PR on the walls of the tube downstream. The average thickness of this coating was about 3500 angstroms (Å), corresponding to an average solid matter destruction efficiency (by the downstream plasma) of about 85%. In comparison, the destruction efficiency at an applied power of 600 W was about 96%, and thus no distinct dynamic changes in either the phase or the magnitude of the microwave reflection coefficient were detected as a function of time. Because the solid material tends to deposit on the walls of the tubing downstream of the semiconductor substrate, the determination that the solid matter is in fact detected by the microwave circuit (at 300 W) was verified. In instances where "excessive" microwave power (e.g., 600 W) is used to ignite the gas, the solid material is mostly volatilized, and thus no distinct change in signal is detected when phase or magnitude are measured. Correspondingly, there were also no significant deposits formed on the tube walls. Accordingly, there is effectively an upper limit to the input microwave power that can be applied for this type of material detection methodology, unless the material is (either intrinsically or due to the medium used) more resistant to disintegration or volatilization by the plasma.

Figure 3:
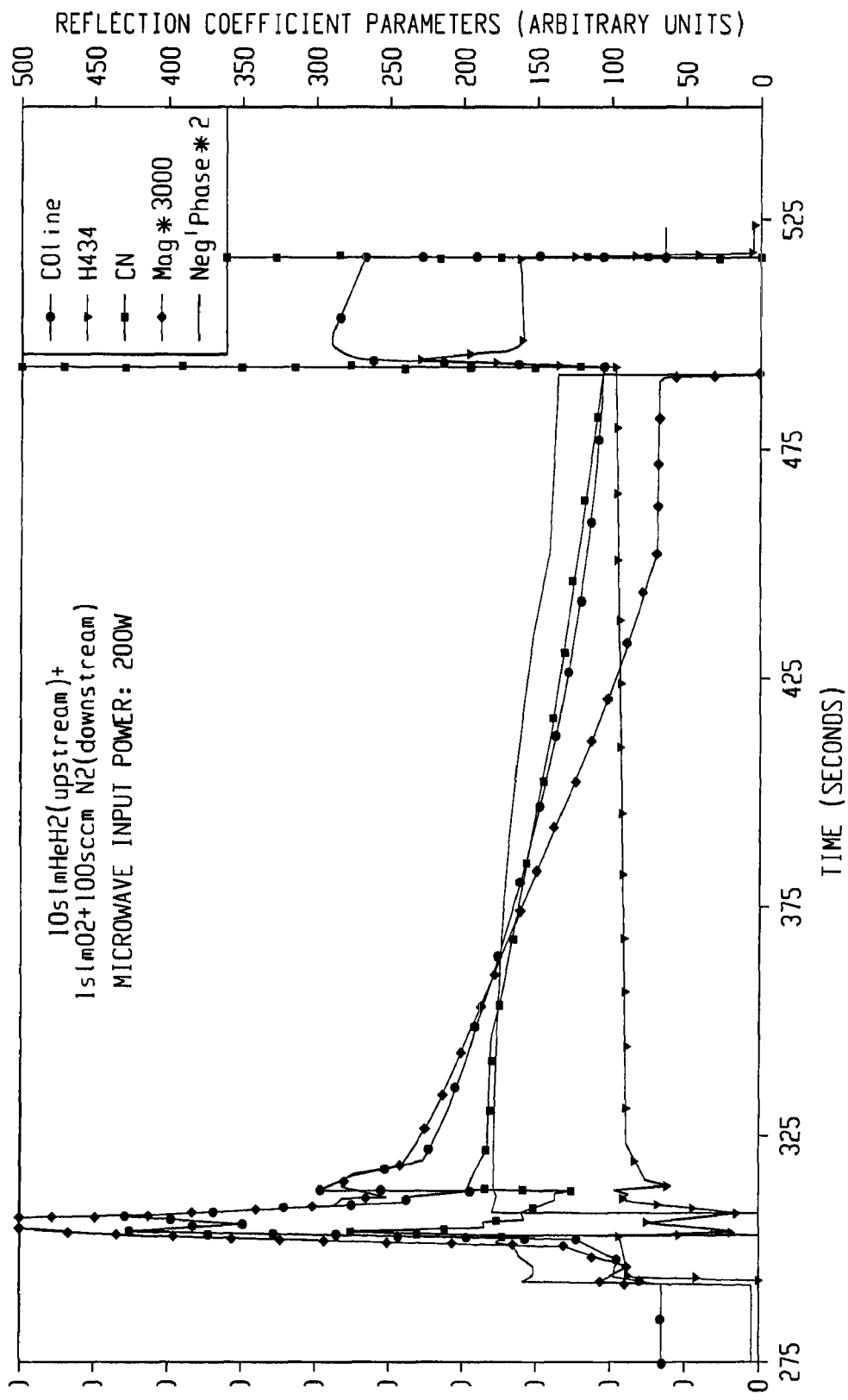
FIG. 3 is a plot illustrating a material detection trial using an applied microwave power of 200 W.
Figure 4:
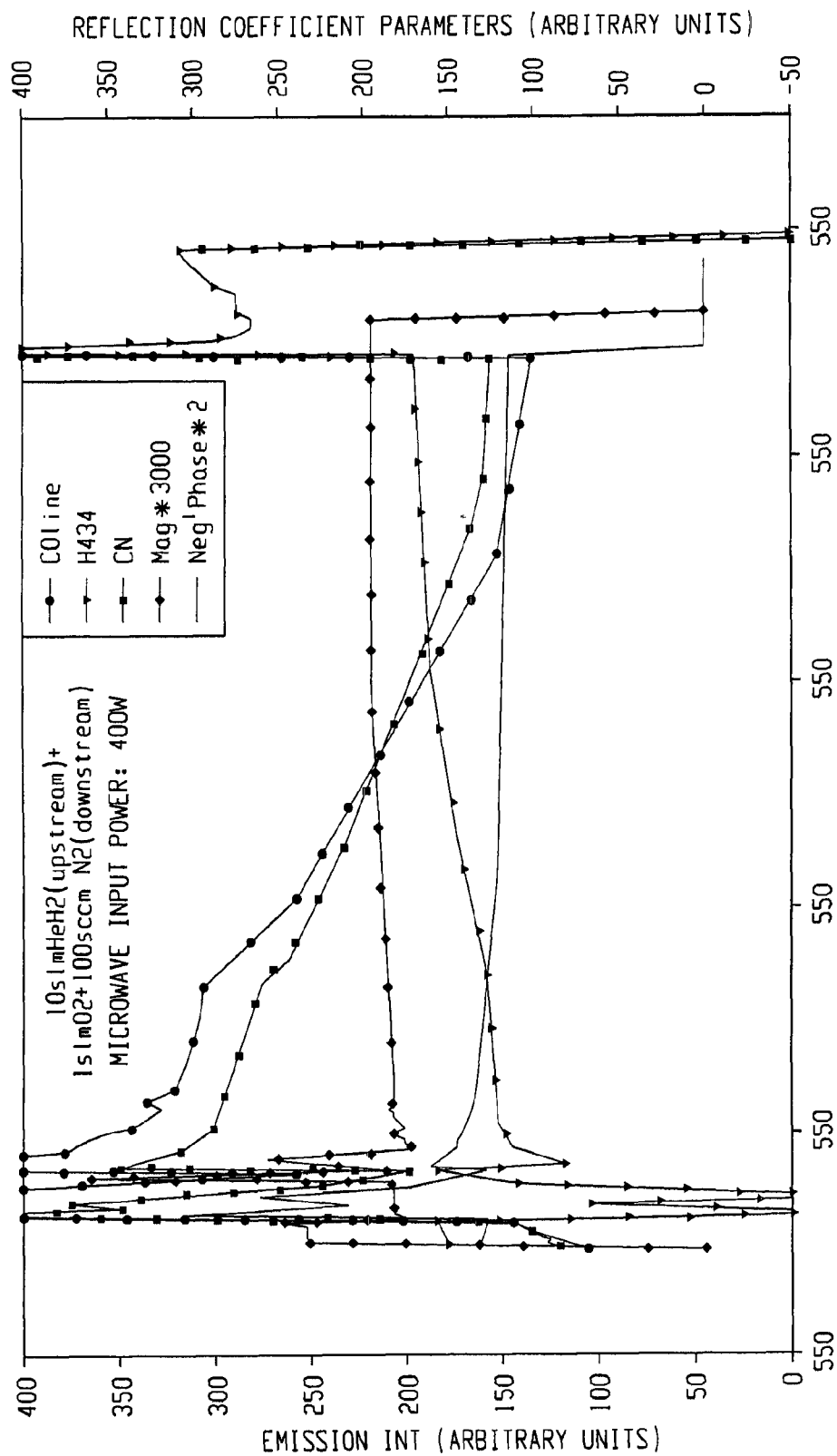
FIG. 4 is a plot illustrating a material detection trial using an applied microwave power of 400 W.

By way of further example, FIG. 3 is a plot illustrating a material detection trial using an applied microwave power of 200 W. Although a decrease in both magnitude and phase as a function of time is generally observed in the microwave circuit, there is a weak correlation of the phase signal to the corresponding CO and CN optical signals, and thus to the amount of solid material in the gas. On the other hand, using an increased applied microwave power of 400 W, there is also demonstrated a weaker correlation of phase and magnitude signals to the optical signals, as shown in FIG. 4. In this example, there is less solid material to detect since the increased power contributes to volatilizing more of the solid material. The power level necessary for the best signal-to-noise in solid material detection can be optimized as needed.

Figure 5:
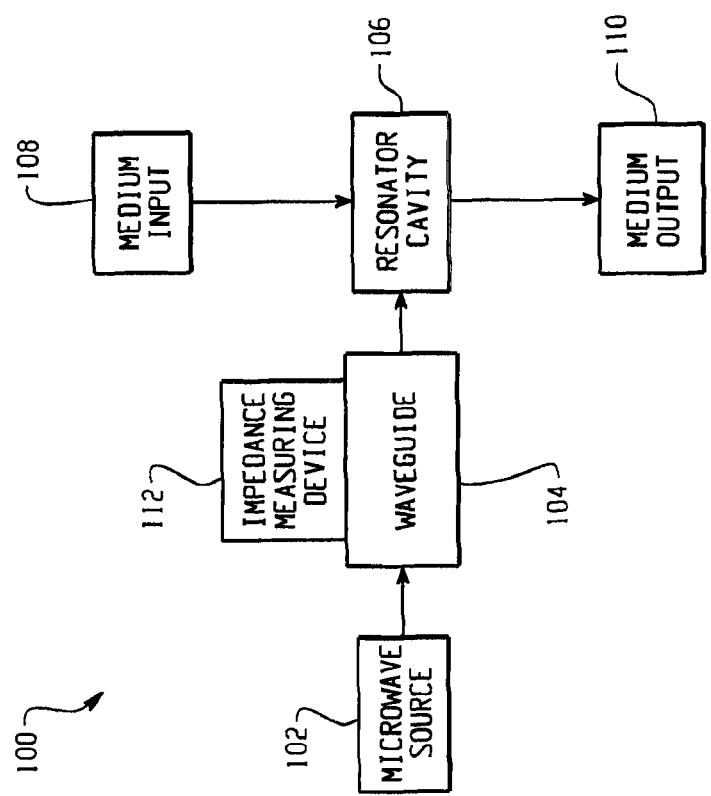
FIG. 5 is a block diagram of a method and system for detection of solid material present within a medium of interest, in accordance with an embodiment of the present invention.

Referring now to FIG. 5, there is illustrated a block diagram 100 of a method and system for detection of solid material present within a medium of interest (e.g., an exhaust gas containing photoresist particulate residue), in accordance with an embodiment of the present invention. Specifically, a microwave power source 102 provides an excitation power source for the medium of interest, and is coupled through a waveguide 104 to a resonant microwave cavity 106. The cavity 106 is further configured so as to receive the medium of interest (e.g., photoresist ashing exhaust gas) therethrough. Thus, the block diagram of FIG. 1 also shows an input side 108 of the medium of interest and an output side 110 of the medium of interest in relationship to the resonant cavity 106. Inside the cavity 106, the medium of interest is excited into a plasma state by the input microwave energy.

At a selected location on the delivery waveguide 104, an appropriate impedance/reflection coefficient measuring device 112 is used to detect, over a given time interval, any change in impedance/reflection coefficient of the microwave circuit thus defined. This in turn provides an indication of the amount of solid particulate material contained within the medium of interest. A suitable impedance-measuring device includes a plurality (e.g., 3 or 4) electric field sampling probes mounted on the centerline of the broadwall of the waveguide 104, and axially spaced at $\lambda_g/6$ or $\lambda_g/8$ intervals, respectively. These electric field samples are then converted to signals that are mathematically transformed into either a reflection coefficient (G magnitude and phase) or an impedance value ($Z=R+/-jX$). This measurement technique is well known to those skilled in the art.

Figure 6:
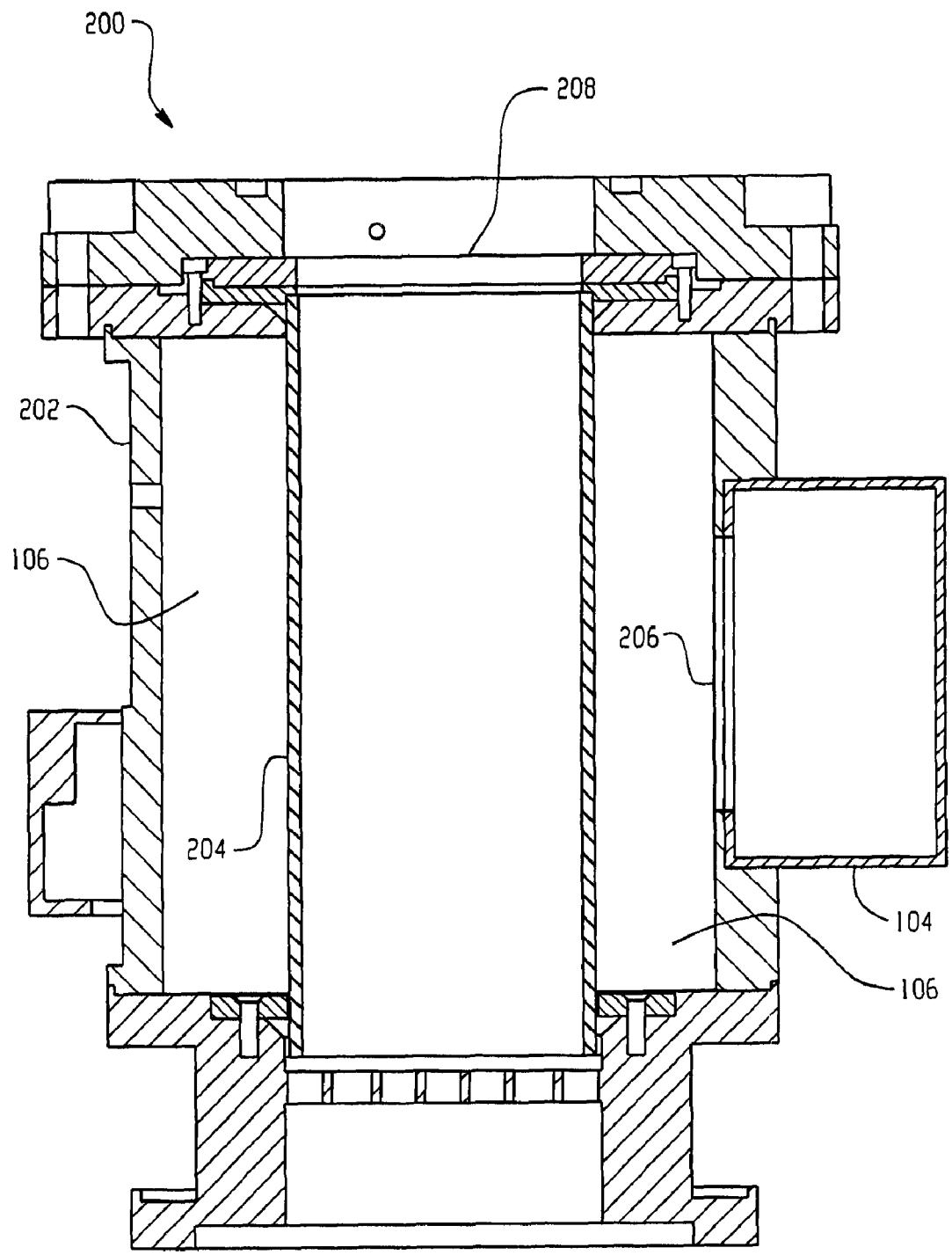
FIG. 6 is a cross-sectional view of an exemplary resonant microwave cavity structure that may be utilized in accordance with an embodiment of the present invention.

FIG. 6 is a cross-sectional view of an exemplary resonant microwave cavity structure 200 that may be utilized as part of a microwave circuit in accordance with an embodiment of the present invention. As is shown, the cavity structure 200 includes a housing 202 in which the resonant cavity 106 is disposed. A plasma transfer tube 204 is positioned inside the cavity 106 for transporting the medium of interest (e.g., upstream exhaust gas) therethrough. The feed waveguide 104 is coupled to the cavity 106 through the broadwall of the waveguide 104 by means of a slot antenna 206, in order to provide an easily accessible axis for initial setup tuning where desired. In addition, an electrically conductive screen 208 allows effluent flow through the resonant cavity 106 while also providing an electromagnetic boundary. In an exemplary embodiment, the microwave cavity 106 utilizes the $TE_{112}$ mode. It should be appreciated, however, that other applications might employ different tube sizes with other propagation modes for the purpose of solid material detection.

Figure 7:
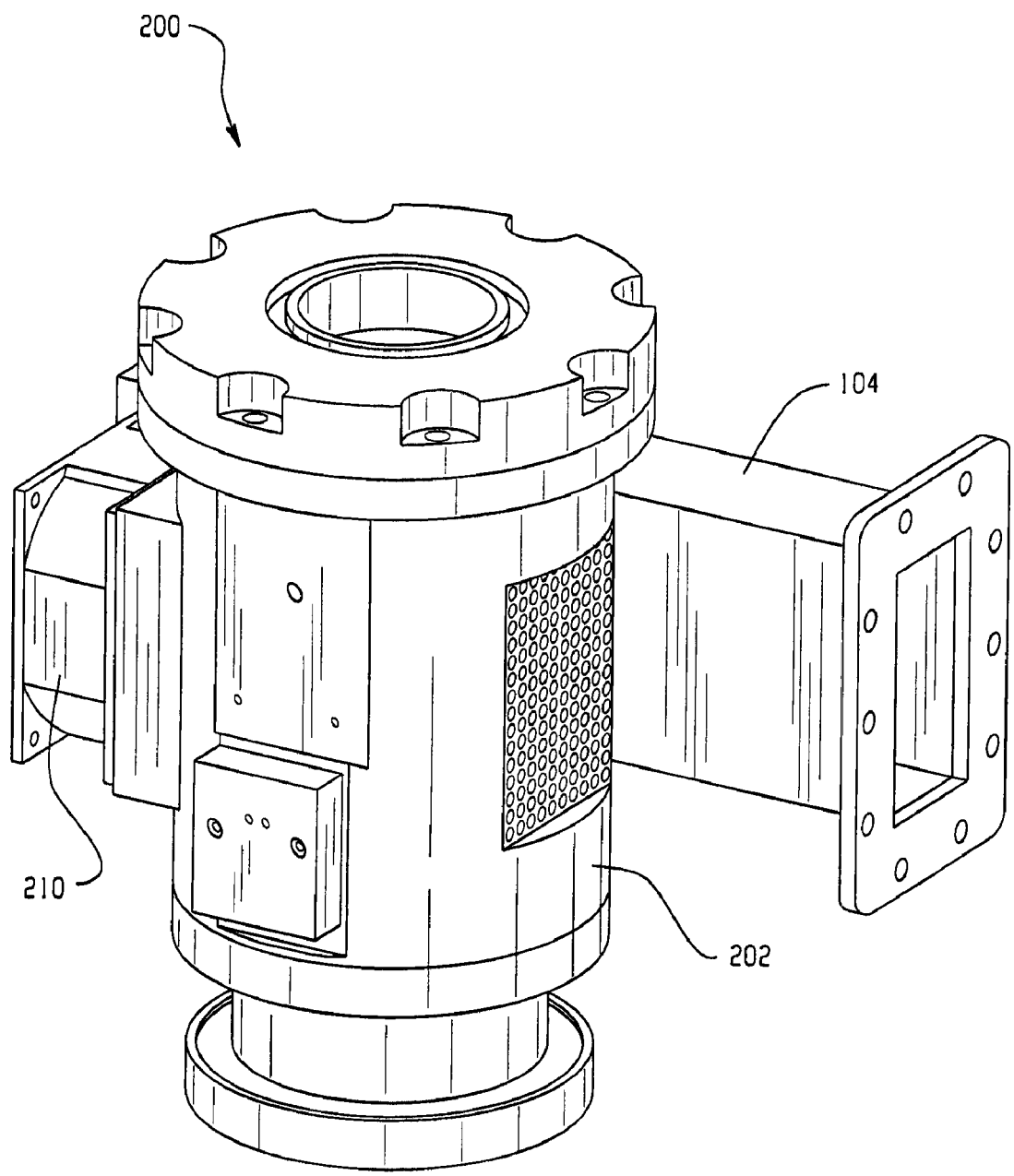
FIG. 7 is a perspective view of the resonant cavity structure shown in FIG. 6.

FIG. 7 is a perspective view of the resonant cavity structure 200 shown in FIG. 6, more particularly illustrating the relationship between the feed waveguide 104 and the cavity structure 200. A magnetron (not shown in FIG. 7) is used as the microwave power source 102 in the present application. A cooling fan 210 may also be utilized in cooling both the magnetron and plasma transfer tube 204.

Figure 8:
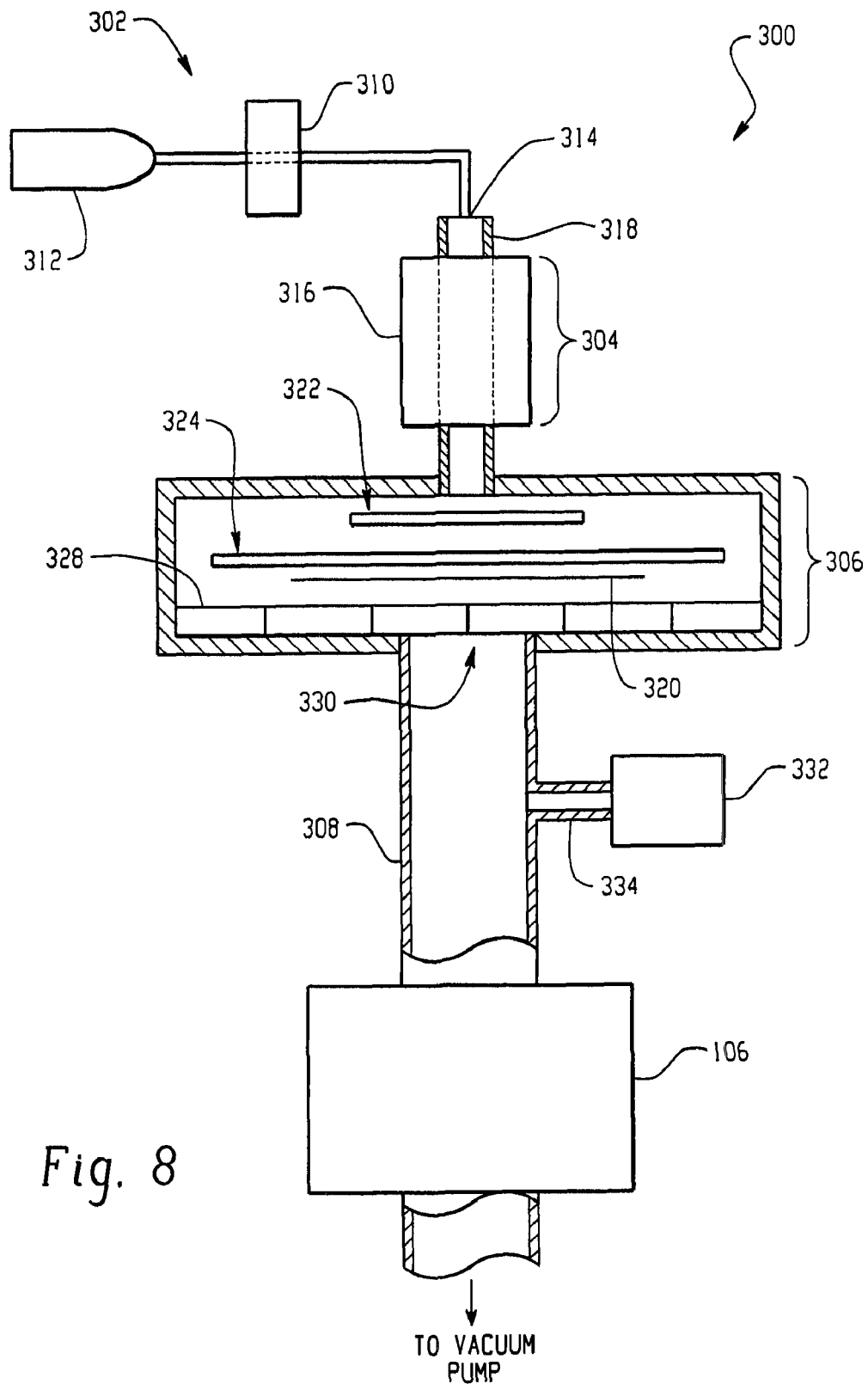
FIG. 8 is a schematic diagram of an exemplary plasma based semiconductor removal apparatus illustrating one particular application for the solid material detection system and method of FIG. 5, in accordance with a further embodiment of the invention.

FIG. 8 is a schematic diagram of an exemplary plasma based semiconductor removal apparatus 300 illustrating one particularly suitable application for the solid material detection system and method of FIG. 5, in accordance with a further embodiment of the invention. Plasma apparatus 300 generally includes a gas delivery component 302, a plasma generating component 304, a processing chamber 306, and an exhaust tube 308 that, in the exemplary application, provides a path for the medium of interest component (e.g., photoresist-containing exhaust gas downstream from a workpiece) that is inputted to a resonant microwave cavity structure described in FIGS. 5 and 6.

The gas delivery component 302 may include a gas purifier 310 in fluid communication with a gas source 312 and a gas inlet 314 of the plasma generating component 304. An additional gas source (not shown) may also be in fluid communication with the gas inlet 314 for providing in situ cleaning capability. The microwave plasma generating component 304 includes a microwave enclosure 316, which is generally a partitioned, rectangular box having a plasma tube 318 passing therethrough. As is known in the art, the microwave plasma generating component 304 is configured to cause excitation of the input gas into a plasma so as to produce a reactive species. In addition to microwave energy, the plasma generating component 304 could also be operated with an RF energy excitation source.

Once excited, the reactive gas species is introduced into an interior region of the processing chamber 306 for uniformly conveying the reactive species to the surface of a workpiece 320, such as a resist-coated semiconductor wafer. In this regard, one or more baffle plates 322, 324 are included within the processing chamber 306. Although the specific manner of operation of the baffle plates is not described in further detail hereinafter, additional information on such operation may be found in Ser. No. 10/249,964, referenced above. In order to enhance the reaction rate of the photoresist and/or post etch residue with the reactive species produced by the upstream plasma, the workpiece 320 may be heated by an array of heating elements (e.g., tungsten halogen lamps, not shown in the figures). A bottom plate 328 (transparent to infrared radiation) is disposed between the processing chamber 306 and the heating elements 326. An inlet 330 of the exhaust tube 308 is in fluid communication with an opening in the bottom plate for receiving exhaust gas into the exhaust tube 308.

As further illustrated in FIG. 8, all of the exhaust gas from the workpiece goes through exhaust tube 308 into the plasma generating component of the solid material detection system 100 (in particular through the plasma transfer tube included within resonator cavity 106), en route to a vacuum pump (not shown in FIG. 8). Optionally, an oxidizing gas source 332 and inlet 334 may be provided to enhance the destruction efficiency of the solid matter.

Again, it should be understood that within the exemplary application (photoresist ashing) discussed, the plasma ashing apparatus 300 represents an example of one such device that could be used in conjunction with the material detection system/methodology disclosed herein, and that other types of apparatus are also contemplated.

It will be appreciated that the correlation between the impedance/reflection coefficient measured in the microwave circuit and the amount of photoresist that is not volatilized may also be used in a dynamic type of endpoint detection. That is, the measurement of microwave impedance/reflection coefficient can be a method of signaling when the components upstream of the microwave circuit in the vacuum line are devoid of resist. Thus, to effectively volatilize the photoresist material while still checking for presence of solid resist material traveling through the conduit in the present embodiment, the applied microwave power could be periodically reduced for very short periods of time (e.g., 100 ms) representing "detection" periods of a duty cycle. As such, during "high power" periods of the duty cycle, the photoresist would be effectively volatilized, while during brief "low power" periods, the quantity of remaining photoresist material could be detected. The cycle is then repeated by alternating between high and low power levels, until it is finally determined that the photoresist is completely cleared from the substrate upstream.

Figure 9:
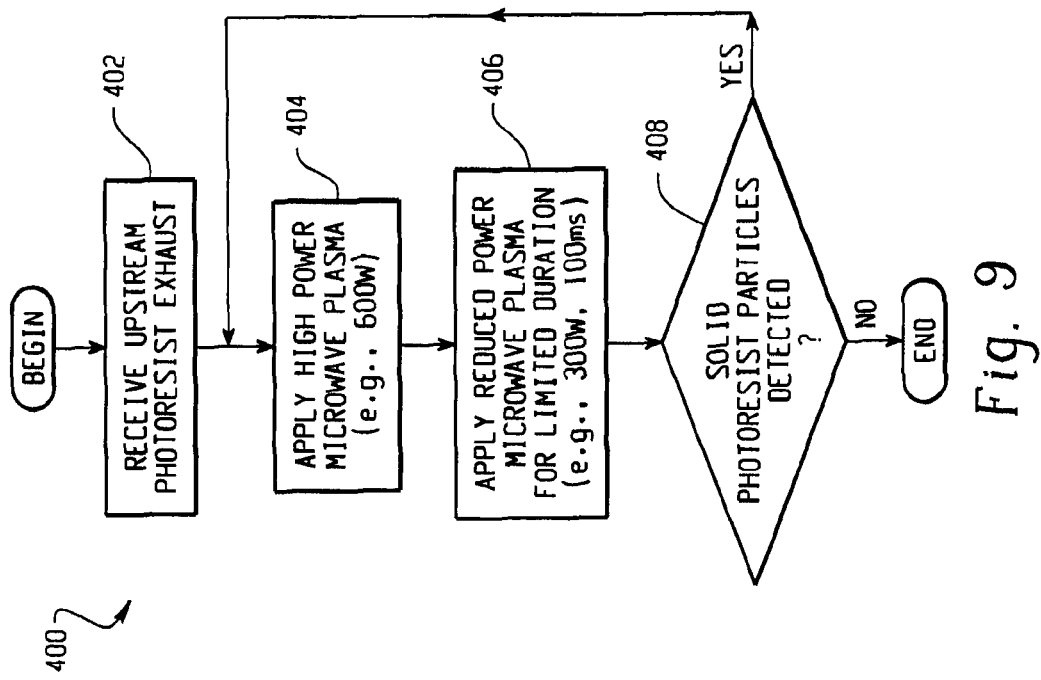
FIG. 9 is a flow diagram illustrating a method for implementing material removal from a semiconductor workpiece, in accordance with another embodiment of the present invention.

Accordingly, FIG. 9 is a flow diagram illustrating a method 400 for implementing material removal from a semiconductor workpiece, in accordance with another embodiment of the present invention. As shown in the diagram, method 400 begins at block 402 by receiving the exhaust gas containing photoresist into a microwave circuit. Then, as shown in block 404, a relatively high power level (e.g., 600 W) is applied to the microwave circuit in order to volatize any photoresist particulate matter contained in the upstream exhaust gas. After a predetermined time at high power, the power level is reduced for a limited duration (e.g., to 300 W for 100 ms), as shown at block 406. This allows for a sensing operation, as discussed above, to see whether solid materials remain in the exhaust. Thus, at decision block 408, if solid materials are still present as detected by the impedance/reflection coefficient measuring technique, then the process is repeated at high power. If no materials are detected, then the endpoint is reached.

It will also be appreciated that the above described impedance/reflection coefficient based material detection techniques may have applicability in other areas such as, for example, detection of solid materials in the exhausts of solid waste destruction systems (e.g., incinerators), detection of particulates in the exhaust/ventilation systems of industrial facilities (e.g., paper industry, coal-based power generation plants, etc.), detection of bulk contaminates for gas delivery systems, detection of particulates in the atmosphere by means of a balloon or other transport mechanism, as well as for detection of particulates in etching/CVD chambers in the semiconductor manufacturing industry.

While the disclosure has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for detection of solid materials present within a medium of interest, the method comprising:
configuring the medium of interest within an electromagnetic circuit;
exciting the medium of interest using electromagnetic energy; and
determining an impedance value of said electromagnetic circuit, wherein said impedance value corresponds to an amount of solid material within the medium of interest.

2. The method of claim 1, wherein said electromagnetic circuit further comprises at least one of a microwave circuit and a radio frequency (RF) circuit.

3. The method of claim 1, wherein the medium of interest is excited into a plasma state by at least one of a microwave energy source and an RF source.

4. The method of claim 1, wherein said determining an impedance value further comprises determining a reflection coefficient magnitude value and a reflection coefficient phase value.

5. The method of claim 4, further comprising determining variations of said reflection coefficient magnitude and phase values over time.

6. A method for solid material detection in a photoresist removal system, the method comprising:
receiving an exhaust gas downstream with respect to a workpiece from which a photoresist material is removed;

configuring an electromagnetic circuit to include said exhaust gas;

exciting said exhaust gas using electromagnetic energy; and determining an impedance value of said electromagnetic circuit, wherein said impedance value corresponds to an amount of solid material within the exhaust gas.

7. The method of claim 6, wherein said electromagnetic circuit further comprises at least one of a microwave circuit and a radio frequency (RF) circuit.

8. The method of claim 6, wherein said exhaust gas is excited into a plasma state by at least one of a microwave energy source and an RF source.

9. The method of claim 6, wherein said determining an impedance value further comprises determining an impedance magnitude value and an impedance phase value.

10. The method of claim 9, further comprising determining variations of said impedance magnitude and phase values over time.

11. The method of claim 9, wherein said electromagnetic energy is applied at a power of about 200 watts (W) to about 400 W.

12. The method of claim 9, wherein said electromagnetic energy is applied at a power of about 300 watts (W).

13. The method of claim 9, further comprising utilizing said determined impedance values for endpoint detection of removal of said photoresist material.

* * * * *